(12) United States Patent
Heywang-Koebrunner et al.

(10) Patent No.: US 7,758,601 B2
(45) Date of Patent: Jul. 20, 2010

(54) METHOD FOR EXAMINING TISSUE SAMPLES AND DEVICE THEREFOR

(76) Inventors: Sylvia Helen Heywang-Koebrunner, Eicnhoernchenweg 9, Baldham (DE) 85598; Walter Heywang, Schwabener Weg 9a, Grasbrunn (DE) 85630

( * ) Notice: Subject to any disclaimer, the term of this patent is extended or adjusted under 35 U.S.C. 154(b) by 0 days.

(21) Appl. No.: 12/015,139

(22) Filed: Jan. 16, 2008

(65) Prior Publication Data
US 2008/0132805 A1 Jun. 5, 2008

Related U.S. Application Data

(63) Continuation of application No. PCT/EP2006/007066, filed on Jul. 18, 2006.

(30) Foreign Application Priority Data
Jul. 18, 2005 (DE) .................... 10 2005 033 474

(51) Int. Cl.
*A61B 17/32* (2006.01)
*A61B 10/00* (2006.01)
(52) U.S. Cl. ................ 606/171; 600/566; 600/567
(58) Field of Classification Search ......... 600/562–568; 606/170, 171
See application file for complete search history.

(56) References Cited

U.S. PATENT DOCUMENTS

| 4,500,507 | A | * | 2/1985 | Wong ........................ 424/1.65 |
| 4,718,417 | A | | 1/1988 | Kittrell et al. |
| 5,078,142 | A | | 1/1992 | Siczek et al. |
| 5,524,634 | A | * | 6/1996 | Turkel et al. ................ 600/562 |
| 5,775,333 | A | | 7/1998 | Burbank et al. |
| 5,876,711 | A | * | 3/1999 | Fattaey ...................... 424/93.2 |
| 5,928,164 | A | * | 7/1999 | Burbank et al. ............. 600/567 |
| 5,983,125 | A | | 11/1999 | Alfano et al. |
| 6,296,608 | B1 | * | 10/2001 | Daniels et al. .............. 600/104 |
| 6,485,436 | B1 | * | 11/2002 | Truckai et al. .............. 600/564 |
| 6,978,788 | B2 | * | 12/2005 | Klimberg et al. ............ 128/898 |
| 7,192,404 | B2 | | 3/2007 | Rhad et al. |
| 7,359,550 | B2 | * | 4/2008 | Brand ........................ 382/181 |
| 2001/0017137 | A1 | * | 8/2001 | Burbank et al. ............. 128/898 |
| 2001/0047135 | A1 | | 11/2001 | Daniels et al. |
| 2003/0125640 | A1 | | 7/2003 | Klimberg et al. |

(Continued)

FOREIGN PATENT DOCUMENTS

EP 1 319 568 A2 6/2003

(Continued)

*Primary Examiner*—Max Hindenburg
*Assistant Examiner*—John Pani
(74) *Attorney, Agent, or Firm*—Slater & Matsil, L.L.P.

(57) ABSTRACT

For examining tissue samples that were taken from a tissue area with suspicion of tumor it is proposed that the tissue samples be examined shortly afterward for a measurement value typical of tissue alteration. With tissue samples taken spatially-systematically, a measurement value distribution at the sampling site can be ascertained, and an image of the tissue alteration before sampling can be represented. The device for performing the method includes a sampling device (PU), a supply device (TU), a detector (Det), an evaluation unit (CPU), a storage unit (SU) and an output device (AV) that allows an online examination of taken tissue samples (Pr), and with which the three-dimensional image can be represented by, for instance, a distribution at the sampling site of fluorescence achieved by means of systemically applied markers.

35 Claims, 2 Drawing Sheets

U.S. PATENT DOCUMENTS

2004/0030263 A1 2/2004 Dubrul et al.
2005/0095666 A1 5/2005 Jhavar et al.

FOREIGN PATENT DOCUMENTS

| | | |
|---|---|---|
| GB | 2 404 607 A | 2/2005 |
| WO | WO 98/01074 | 1/1998 |
| WO | WO 98/40007 | 9/1998 |

\* cited by examiner

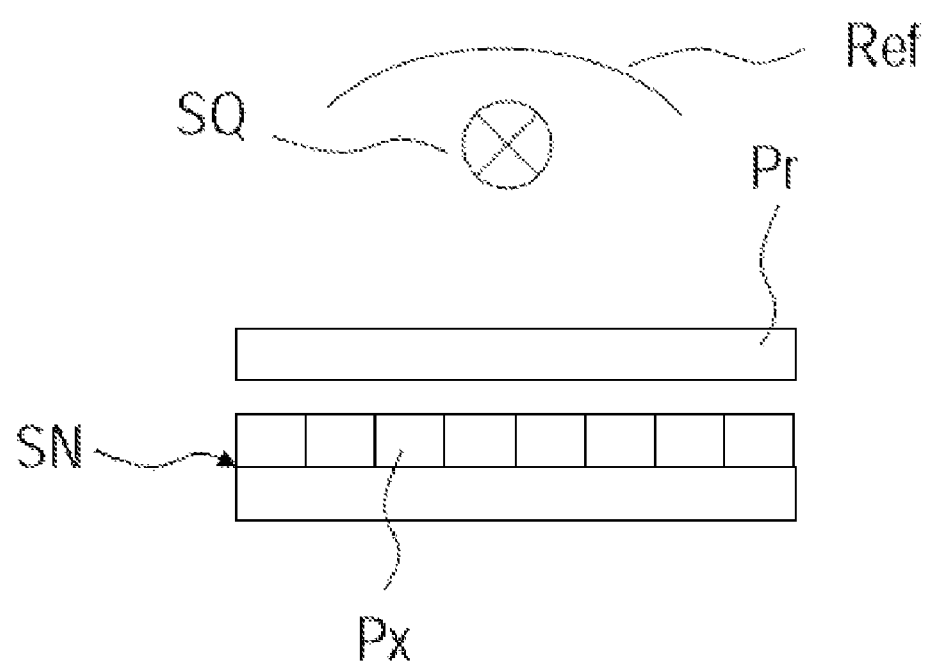

METHOD FOR EXAMINING TISSUE SAMPLES AND DEVICE THEREFOR

This application is a continuation of co-pending International Application No. PCT/EP2006/007066, filed Jul. 18, 2006, which designated the United States and was not published in English, and which is based on German Application No. 10 2005 033 474.1 filed Jul. 18, 2005, both of which applications are incorporated herein by reference.

BACKGROUND

Breast cancer is the most common cancer disease among women and the most common cause of death for women between 35 and 55. Examinations every one or two years for early detection of breast cancer are therefore recommended for women. Mammography, clinical examination (including palpation) and ultrasound examinations are used for primary diagnosis of breast cancer.

Magnetic resonance imaging is another diagnostic instrument, which has a high sensitivity to abnormalities but only a low specificity and resolution. It is also disadvantageous that this is an expensive procedure, which is not suited for routine examinations.

If conspicuous but not unambiguous abnormalities are found with these methods then tissue samples, which are then histologically examined, can be taken by means of a core needle biopsy or an aspiration biopsy. Although a tissue volume above 20 mm in diameter can now be removed by aspiration biopsy, it has so far only been used for diagnostic purposes and for the removal of unambiguously benign tumors, since a sufficiently secure monitoring with regard to a complete removal of the tumor is not possible with the described method.

SUMMARY OF THE INVENTION

Aspects of the present invention provide further development of minimally invasive biopsy methods, in particular aspiration biopsy, with regard to a simpler and secure monitoring of the knowledge obtained with it. For example, embodiments of the present invention specify a method and a device with which tissue samples can be easily and rapidly examined for pathological tissue alterations, e.g., carcinomas.

In one embodiment, a method for representing and/or recognizing tissue alterations in tissue samples is disclosed. Starting from a number of tissue samples (Pr) associated with coordinates (z, r, phi) of a respective sampling site, these tissue samples are examined for at least one parameter and any tissue alteration that may be present is recognized or measured. An image of the tissue alteration at the sampling site is obtained before the sampling.

BRIEF DESCRIPTION OF THE DRAWINGS

The invention will be described in detail below on the basis of embodiments and the associated figures. The figures serve solely to illustrate the invention and are therefore only executed schematically and not to scale. Identical or identically functioning components are labeled with identical reference characters.

FIG. 3 shows a detector that is a part of the device in a schematic cross-section.

Figure 1:
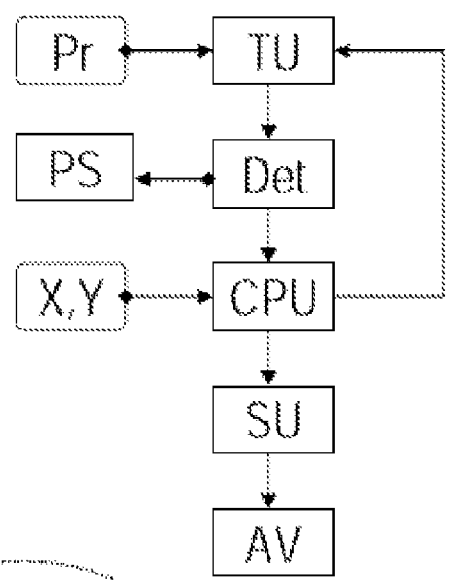
FIG. 1 shows a process diagram of the method.

The following list of reference characters is used in conjunction with the drawings.

| | |
|---|---|
| Pr | Tissue sample |
| Nd | Core needle |
| Cy | Rotatable inner cylinder |
| Oe | Opening |
| PU | Sampling device |
| TU | Supply device |
| Det | Detector |
| Ref | Reflector |
| SQ | Radiation source |
| SN | Sensor |
| Px | Sensor element |
| CPU | Evaluation device |
| SU | Storage unit |
| AV | Output device |
| IN | Input device |
| PS | Sample storage |
| Ref | Reflector |
| K | Body |

DETAILED DESCRIPTION OF ILLUSTRATIVE EMBODIMENTS

It is proposed to examine a number of tissue samples to which respective sampling sites have been assigned in the form of coordinates for at least one parameter characteristic of a tissue alteration, and thus to obtain an image of the tissue alteration at the sampling site before sampling, and therefore unchanged by the sampling.

In particular, the examination is carried out a short time after the sampling so that the examination can take place virtually online in the limiting case.

Tissue samples taken in a minimally invasive manner are preferably used. A method suitable for this is aspiration biopsy. This is suitable for spatially systematic taking of tissue samples so that assignment to the sampling coordinates, the coordinates of the sampling site, to the tissue samples is possible already during the sampling. Sampling coordinates in the sense of the invention are understood to mean the coordinates in the tissue that the tissue sample occupied before any removal.

In this manner, an image of the tissue alterations in their original state before sampling can be obtained from the examination. In particular, the spatial shape or the spatial extent of the tissue alterations can be recognized and determined in this way as a two or three-dimensional image. This opens the possibility of obtaining additional knowledge regarding tissue alterations.

In aspiration biopsy, a core needle having a wide opening laterally approximately 5-10 mm from its tip, through which adjacent tissue can be drawn into the core needle by means of negative pressure, is guided to the sampling site. The opening is then closed off by a sharp blade on the inside wall of the needle, the aspirated tissue thus being cut off. The cylinder with cut-off tissue is then transported out of the body through the core needle by a second aspiration at its end. By rotating the core needle about its own axis, tissue cylinders can analogously be taken from all directions around the core needle. With continuous sampling, a tissue volume of up to about 2 cm in diameter can thus be sampled. The inventive method begins only after this step, i.e., with the tissue samples obtained in this way.

The biopsy needle can serve as the axis of a cylindrical coordinate system (translation=z, radius=r, rotation=phi), wherein the coordinates of the respective sampling site can then be determined or obtained.

The sampling site can be established as follows. The core needle itself is previously introduced, under the control of an imaging process, preferably centrally into a suspected area of the tissue to be examined of the specific patient to be examined, and remains there until all desired tissue samples have been taken. It thus serves as a fixed center. It is then rotated step-by-step so that the sampling window faces in a different direction each time. Alongside the position of the biopsy needle as the center, a first absolute coordinate (phi) of the tissue sample is obtained from the "clock hand indication" in the form of an angle of rotation relative to a starting position. It is also possible to determine the coordinates only relative to the center defined by the initial position of the core needle.

A second coordinate is obtained as the original distance of the sampling site for the tissue sample from the axis. This can be determined advantageously and easily from the number and thickness of the samples taken in this direction. The sampling direction corresponds to the aforementioned angle of rotation relative to an initial positing, which represents a mean value for the angle range that corresponds to the angle of aperture of the sampling window. The two first coordinates already allow a precise position determination in one plane.

Another coordinate (z coordinate) is determined along the cylinder axis. This can be obtained by way of the position of a measurement value in the extended cylinder of the removed sample. The penetration depth of the core needle must also be taken into consideration for the third coordinate, because it can be varied to cover a larger area in the sampling.

Sampling can progress successively with intermediate rotations of the biopsy needle about its axis, and the coordinates of the tissue samples can be determined systematically and easily.

It is advantageous to fix the tissue during the entire sampling. This prevents changes of position, particularly in soft, yielding tissue such as the breast and allows the preparation of an accurate and undistorted image of the tissue alterations as they existed prior to the sampling. For the breast, the fixation can be accomplished by breast compression, for example.

The image obtained from the measurement values for the parameter and the associated coordinates can be presented on an output device (e.g., with a 2D or 3D display). Grayscales, color codes or color gradations can be used for a graphic representation of the at least one measured tissue parameter, in order to represent a degree of alteration. It is also possible however, to detect only the presence of the alteration and thus to present an image comprising only two states, for instance. This is significant if, for example, measurement values below a predetermined threshold are to be suppressed so that it is only displayed whether the threshold is reached or not at a given position. The threshold suppression can also be combined with the color codes or the color gradations. The representation can be output on a monitor, a projector or a printer, optionally connected directly to the system. In particular, sectional images with arbitrary orientation can also be obtained from the dataset.

In embodiments of the inventive method, tissue samples taken according to a preferably spatially symmetric procedure can be serially aspirated into a tube or a chamber system, and the thus-obtained ordered state can represent at least a part of the association process to the sampling site. Thus the sampling and the measurement of the parameter can be decoupled.

In embodiments of the inventive method, a parameter can be examined that represents a naturally existing tissue property of an altered metabolism. For this purpose the tissue samples are normally optically detected, for example, wherein a reflective or absorbed wavelength or in general a transparency can be determined. For instance, the altered phosphocholine content can be determined.

It is also possible to further label the altered tissue before or during the examination for the parameter, for which a so-called marker can be used. For this purpose, a substance that becomes concentrated in the altered tissue is supplied or imparted to the tissue. For example, the marker can be systemically administered (orally or by injection) prior to the sampling at time intervals characteristic of the marker or its mode of operation. It is then concentrated primarily in pathologically altered tissue, e.g., in tumors. A certain marker concentration may possibly also be measured in healthy tissue (depending on the marker used), but it is markedly below that of tumor tissue. To improve the representation, a threshold value can therefore be input, below which the representation of intensity at the output device is suppressed. Assuming that an altered focus leads to a marked increase of the measurement value in the sampled tissue, a spatial representation of the focus in its spatial dimensions is successfully accomplished in this manner. Additional interesting information on the type and propagation of the focus (e.g., shape and margin as typical of tumor growth or type) can also be obtained in this manner.

The alteration labeled by the marker can also be optically verified. A secondary radiation caused by the altered tissue or the concentrated marker therein, such as fluorescence, or radioactive decay if the marker is a radionuclide, can be detected in the exploration. For example, it is possible to use organometallic complexes having a suitable fluorescence with a variety of central atoms such as gadolinium.

It is particularly advantageous if a marker is used with which a localization of the tissue alteration before the biopsy is possible. Then the patient need only be treated once with the marker. A different characteristic of the marker can be used for tissue characterization than for primary localization, so-called radiolocation of the lesion. Suitable combinations with substances (markers) known to be suitable for this purpose are, for instance, contrast agents for X-ray or MRI examinations that simultaneously emit fluorescent light. However, characteristics recognizable by means of other detector systems can also be combined in markers and used in the proposed method.

If more than one parameter is determined in the examination of the tissue samples, then the different spatially coordinated measurement values can be linked and, in particular, overlapping images from the measurements for two or more parameters can be generated. From the image information thus determined, in particular, in an automated process, additional interesting knowledge for the examiner can be determined.

The preparation of a dataset on the spatial distribution of the measured tissue alteration is successfully accomplished in a simple manner with a series of tissue samples obtained by means of aspiration biopsy. The coordinates to be assigned to the samples result from a running sample number Np and an angle $\alpha_n$, increasing in predetermined, preferably constant steps $\Delta\alpha$. The needle or its inner cylinder is rotated by this angle $\Delta\alpha$ between the taking of two tissue samples with consecutive sample numbers. All rotations are preferably in the same direction.

For each tissue sample a track number n is calculated, beginning with n=1, that increases by one after each full revolution, i.e., whenever the angle of rotation $\alpha_n$ exceeds an integer multiple of 360°. It is assumed that the respective tissue samples associated with a single track number n have the same distance from the core needle. Track refers to all positions in the tissue that are an identical distance away from the needle. From the angle of rotation an and the track, a distance r and a sector at the sampling site are subsequently assigned to each tissue sample. The angle of rotation of two successive tissue samples then differs by the aforementioned angle $\Delta\alpha_n$, which corresponds to one revolution of the window on the sampling instrument. The rotation between two samplings preferably differs by the angle corresponding to the aperture angle of the sampling window. This is 30-60°, for example In further elaboration of the method, it is possible to increase the number of tissue samples taken per track as the number of tracks n increases. Within a single track, there is a rotation about the same angle between each two samplings. A different progression of the sampling is also possible. What is relevant is the unambiguous association of the tissue samples to their original coordinates before tissue was removed.

Contrast agents already approved for MRI are, for instance, gadolinium chelate complexes and in particular Gd(DTPA), which has diethylenetriamine pentaacetate as a chelating agent. This Gd-DTPA is available commercially as Megluminsalz in aqueous solution with a concentration of 500 nmol/L. It can be administered intravenously and first distributes itself in the intravasal area, but moves rapidly into the extracellular space. The high magnetic moment of the $Gd^{+++}$ ion allows observation via MRI. The $Gd^{+++}$ is shielded by the chelate and is not toxic. At the same time, Gd(DTPA) has optical fluorescence properties which have so far not been utilized with this medical contrast agent. Comparable fluorescence can also be expected with other (already approved) MRI contrast agents (other Gd complexes or complexes with other rare earths). In addition, metalloporphyrins that can be administered orally are suitable as optical fluorescent markers. Also suitable as fluorescent markers are fluorescence-labeled bacteria, viruses or proteins, insofar as they preferentially settle in tissue with tumor activity. Altered tissue is also successfully labeled with genetically engineered organelles or proteins. Thus, luminescent or fluorescent bacteria or viruses which not only accumulate in altered tissue, but also reproduce can be used as markers.

It is not only possible to recognize and/or display a tissue alteration with the present method but also to combine it with the removal of all tissue with recognized alterations on the basis of the online method now possible. It is then possible to remove all altered tissue safely and completely in a minimally invasive manner, with recognition and removal taking place with the same instruments, in this case a core needle for aspiration biopsy, with only one invasive procedure.

It is possible to proceed as follows, for example:
a biopsy instrument with a sampling window is placed in the altered tissue and a first sample set corresponding to one tissue layer (track) is systematically taken around the instrument,
the tissue samples are examined virtually online immediately after sampling,
additional tissue samples are taken in the direction in which alterations were observed in the first sample set, and
the process of tissue removal and sampling is continued until no more tissue alterations are found in the tissue samples.

For complete removal of altered tissue, a safety margin of tissue, wherein no alteration can be detected, is subsequently removed in all directions relative to the center.

A device for performing the method, and correspondingly for obtaining three-dimensional data from tissue samples, comprises a sampling device constructed such that it enables a spatially associable removal of tissue samples, and an examination unit that is constructed for immediate examination of the removed tissue for selected parameters.

In one refinement, the device also comprises a controller that can adjust the removal of additional tissue samples as a function of a program and/or the results of the examination for tissue alterations that has been performed. It advantageously also comprises a supply device for virtually online supply of tissue samples from the sampling device to the examination device, i.e., for transport from the biopsy site to the analysis site.

The examination unit comprises one or more detectors for determining a measurement value of one or more parameters typical of tissue alteration. If this alteration is recognizable by means of fluorescence, then the following is additionally provided:
a radiation source, in particular for short-wavelength light, in the examination unit that can excite a given fluorescence marker inside a tissue sample to fluoresce,
a detector that allows a one-dimensional determination of the intensity of the fluorescent light emitted by the tissue containing the concentrated fluorescent marker, and
an evaluation unit that links the two-dimensional position association of the tissue samples to the intensity of the fluorescent light determined along the sample axis, and optionally to a position change of the core needle along its longitudinal axis (altered penetration depth), and supplies a three-dimensional dataset with the intensity distribution of the fluorescent light at the sampling site.

The biological tissue can be of human or animal origin and can be taken from the living or the dead organism. The radiation source can preferably generate a short-wavelength monochromatic light, and is for instance an LED or a discharge lamp. The detector is designed for one-dimensional determination of the intensity distribution and comprises a point, line or surface detector, optionally movable relative to the sample, in order to detect the aforementioned one-dimensional intensity distribution.

Additionally, an input device is provided by means of which standard values, sampling schemes or two-dimensional coordinate sets of tissue samples can be input. Parameters of the graphic display can also be varied with the input device, or a desired two-dimensional representation based on a section plane can be selected.

The device can further comprise a supply device with which samples can be transported virtually online from the sampling device to the detector device consisting of a light source and a detector. The supply can be performed in constant time intervals, with the measurement of the parameters such as fluorescent activity or its distribution likewise taking place virtually online and being performed, for instance, online in connection with the tissue sampling. In this case the data regarding the position of the sampling window when the sample was obtained can be transmitted as well.

In a simple embodiment for the determination of fluorescence, the detector comprises a photosensitive sensor and a drive unit that can perform a relative motion between the tissue sample and sensor in order to obtain a series of measuring points along the z coordinate, which corresponds to the longitudinal axis of the cylindrical tissue sample. It is advantageous to use detectors, however, that can measure a spatially resolved intensity distribution.

In a further elaboration, the device comprises a light source for short-wavelength light that can be introduced through the core needle to generate a fluorescence at the sampling site, and an optical fiber for detecting the fluorescence produced on site, which is therefore accessible to direct observation by the examiner. He can thus carry out a subsequent check at the sampling site. This can correspond to a visual examination of tumor tissue with regard to heightened fluorescent activity.

With the device it is possible to examine a conspicuous tissue alteration at the sampling site for a parameter typical of it or, one imparted by means of markers, for example, and therefore to examine it for tumor activity, and simultaneously to use the result of the examination to limit tissue sampling to the altered and thus tumor-active region.

Since the detection of the tissue alteration can be done on an automated basis and in real time, the sampling can also be fully automated in such a manner that additional sampling need be performed only in those spatial directions in which an enhanced level of tissue alteration was determined. The automatic controller can be set up such that a safety margin, having a width of, e.g., about 0.5-1 cm depending on requirements or the aggressiveness of the tumor, is peeled out around altered tissue. Tumor tissue and normal tissue can be automatically distinguished by the above-mentioned threshold value, e.g., the threshold value for fluorescent activity.

The automatic controller can be set up such that an angle of revolution $\alpha_n$, composed of the number of individual revolutions by $\Delta\alpha$ and a sequential track number n, is assigned to the samples during the sampling, n corresponding to a whole number greater than zero. A tissue sample is only taken with an increasing angle of revolution if the track number n is 1 or if an alteration was detected in a previous tissue sample with a congruent angle of revolution $\alpha_n$ and a track number n-x, where x and thus the number of safety tracks without alteration to be cut out can be selected freely. For example, a safety margin of about 1 cm can be sent, and x can be correspondingly specified. This consequently implies that, starting from a central axis, samples are taken only in the spatial directions in which fluorescent-active tissue was previously determined.

In another implementation, the device comprises a heat source that can be introduced through the core needle. With the latter it is possible to perform a local application of heat at the sampling site after removal of tissue considered pathological in order to kill possibly surviving tumor cells by means of this thermal treatment. The heat can be applied such that a hyperthermia occurs, i.e., a local heating above the temperature at which pathological cells die.

Using gadolinium chelate complexes for producing a systemic agent with which fluorescence labeling on removed tissue samples is possible also lies within the scope of the invention. Using metalloporphyrins for producing a systemic agent that is concentrated in tumors and can be detected on removed samples by means of fluorescence also lies within the scope of the invention. Use of fluorescence labeled bacteria, viruses or proteins can also serve according to the invention to produce a systemically administrable agent for concentration or detection of pathological tissue in removed samples.

Referring now to the Figures, FIG. 1 shows a schematic process diagram of a method for examining tissue samples. The method starts with tissue samples Pr, from a female breast, for example, which are obtained by means of an aspiration biopsy, for instance. The tissue samples are either taken systematically according to a defined scheme that permits an association to coordinates around the original position of the biopsy device rotatably seated at the sampling site, or are associated as individual samples to the specific position coordinates of the sampling site. These samples are preferably supplied individually and one after the other by means of a supply device TU to a detector Det. The samples, generally present in the form of elongated cylinders, are examined there for a parameter typical of tissue alterations. For instance, tissue areas irradiated by a radiation source show a fluorescent radiation intensity that corresponds to the marker concentration there.

The sensor determines the parameter along the longitudinal axis of cylindrical sample Pr. These data are supplied to a central evaluation unit (CPU). As additional data, the known position coordinates of the tissue samples at the sampling site are supplied to the evaluation unit and are linked there to the intensity distribution along the z coordinate, corresponding to the longitudinal axis of the cylinder. Thus a measurement value distribution in a spatial volume corresponding to the size of the sample is obtained at the sampling site and stored in a storage unit SU. The sample is then transferred from the detector into a sample storage system PS that is constructed for systematic deposition or storage of tissue samples. Then the next sample is brought into the detector by means of supply device TU and measured there.

Whenever a desired number of samples Pr have been examined and their measurement values have been associated with the coordinates, these data can then be output to an output device AV. A monitor on which the progress of the process, or the representation of the intensity distribution, can be followed virtually online, is particularly suitable for this purpose. Alternatively or as an additional output device, a printer can also be connected.

Figure 2:
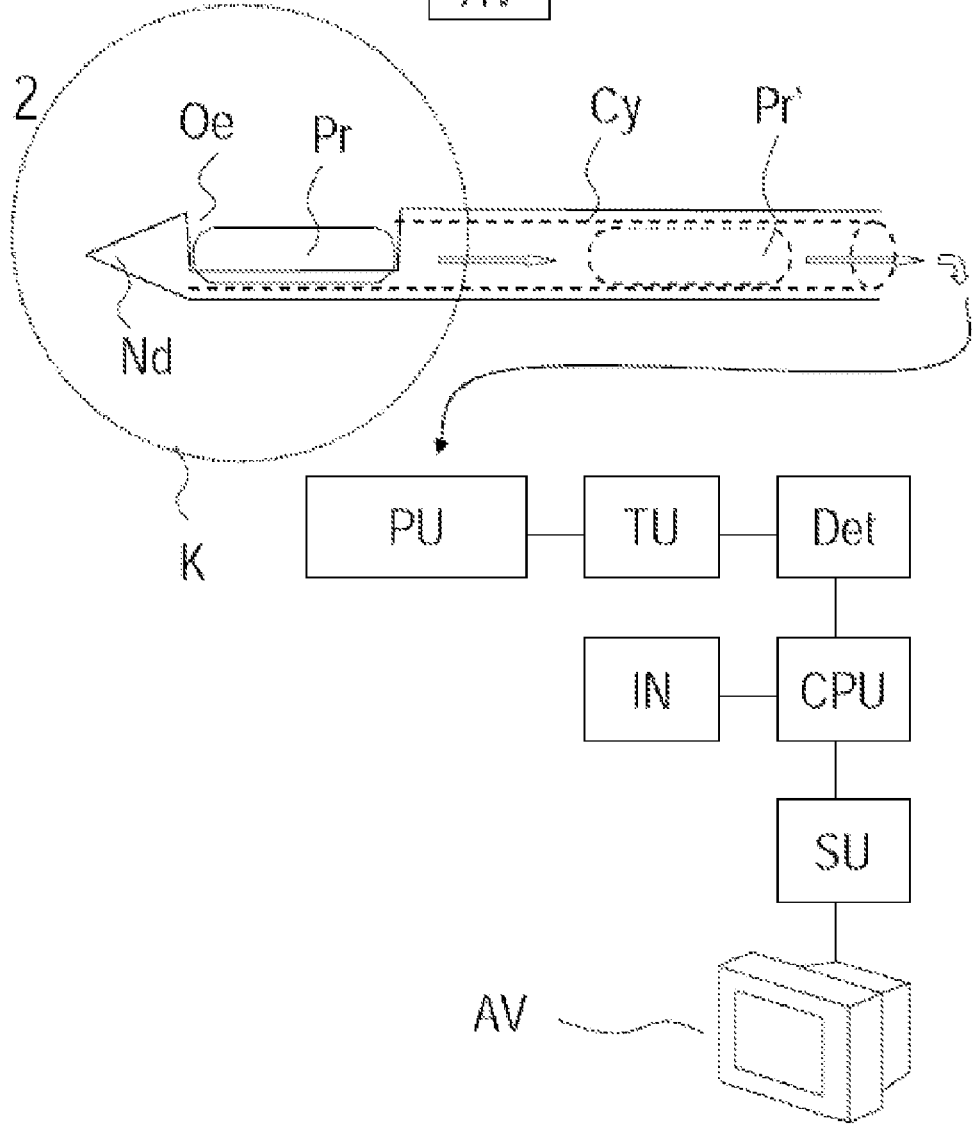
FIG. 2 shows a device for carrying out the method.

FIG. 2 shows a device suitable for performing the method. It comprises the conventional sampling device PU, for instance the aspiration biopsy device, as is distributed by the Ethicon Co. under the name Mammotome®. It includes a core needle Nd and a rotatable inner cylinder Cy guided therein. The core needle has a tip that facilitates the introduction into the tissue at the sampling site. The tissue or the body K, especially the female breast, into which core needle Nd penetrates, is symbolically represented by a circle. An opening Oe, having an angle of aperture of approximately 90° relative to the rotationally symmetrical inner cylinder is provided on the side of the core needle. At a lateral edge of this opening, rotatable inner cylinder Cy is constructed as a rotating blade. Sampling device PU further comprises a means for generating a negative pressure in order to draw an amount of tissue corresponding to the internal volume of opening OE into core needle Nd. The aspirated tissue sample Pr is subsequently cut off by rotation of the inner cylinder Cy and then conveyed out of sampling device PU through core needle Nd. The path of a sample Pr', indicated in broken lines, in the core needle is illustrated with arrows. Removal by means of sampling device PU takes place mechanically or via a second aspiration, for instance.

A supply device TU that supplies the sample to a connected detector can be directly connected to the sampling device. The detector is adjoined by an evaluation device CPU and a storage device SU and the latter is adjoined by an output device AV.

FIG. 3 shows a section of a possible embodiment of a detector of the type that could be used for detecting fluorescence. It contains a radiation source SQ. A reflector Ref that concentrates the light in the direction of tissue sample Pr can also be provided near the tissue sample. A sensor SN, for instance a sensor line that can detect, simultaneously and spatially resolved, a number of sensor points or pixels Px corresponding to the desired resolution is provided next to the tissue sample. The sensor is designed such that it detects exclusively the light associated with the fluorescence of the fluorescent marker. Since the latter is a longer wavelength than that of radiation source SQ, the light from the radiation source can be blocked by using an edge filter. The data determined by the sensor corresponding to the intensity distribution over the length of sample Pr are subsequently transferred to evaluation unit CPU.

The taking of samples can either be systematic or result-oriented as a function of the measurement values. While a tissue area at the sampling site centered at the biopsy needle is removed in the case of systematic tissue sampling, the cutting of additional tissue samples in the case of result-oriented tissue sampling can be continued only in the direction of those spatial coordinates in which a measurement value indicating tissue alteration or tumor was determined in previous samples. The kind of safety margin that will be cut out by the sampling device around a tissue area recognized as a tumor or suspected of being a tumor can be established by specifying desired limit values using an input device.

As a result of the examination of the tissue samples furnished with spatial coordinates, a three-dimensional image of the tissue area suspected of being a tumor having, for example, fluorescence is obtained. The simultaneous employment of different markers is also possible in order to supply complementary three-dimensional information.

The method has the advantage that it can be carried out under software control in an almost completely automated manner. The method can be performed independently of the sampling device solely with tissue samples, but can also be coupled to the sampling device. The method can be performed in parallel to conventional cytologic examinations, since the samples are neither altered nor destroyed by the method. A cytologic diagnosis can thus supplement the picture obtained with the method and allow additional conclusions in the assessment of the overall data.

What is claimed is:

1. A method for taking and examining tissue samples in a surgical procedure, the method comprising:
   systemically administering a marker orally or by injection;
   laying a core needle with a lateral sampling window in altered tissue from inside a living organism;
   taking a first sample set of tissue samples systematically around the core needle;
   examining the first sample set for at least one parameter so that at least one tissue alteration that may be present is recognized or measured, wherein the at least one parameter to be examined is supplied or imparted to the altered tissue via the marker, which concentrates itself in the tissue alteration, the examining being performed after the first sample set is taken but while the surgical procedure is still occurring and while the core needle remains in the living organism; and
   taking additional tissue samples from inside the living organism and, while the surgical procedure is still occurring and while the core needle remains in the living organism, examining the additional tissue samples outside the living organism, the additional tissue samples taken from a location adjacent wherever alterations are recognized in the first sample set, wherein the taking and examining of the additional tissue samples is continued sufficiently long until no more tissue alterations are found by the examining.

2. The method according to claim 1, wherein taking the first sample set and the additional tissue samples comprises obtaining a number of tissue samples associated with coordinates of a sampling site; and wherein examining the first sample set and the additional tissue samples comprises:
   examining the tissue samples for at least one parameter;
   recognizing or measuring the at least one tissue alteration present in the tissue samples; and
   obtaining an image of the at least one tissue alteration at the sampling site by assigning the tissue alterations to the sampling site.

3. The method according to claim 1, wherein taking additional tissue samples comprises taking samples by aspiration biopsy and wherein the examining takes place close in time to taking the tissue samples.

4. The method according to claim 3, wherein measurement values below a predetermined threshold are suppressed in a representation of a dataset obtained from the recognizing or measuring.

5. The method according to claim 2, wherein the tissue samples are obtained with the core needle, the core needle serving as an axis of a cylindrical coordinate system in which coordinates of the sampling site are obtained.

6. The method according to claim 2, wherein tissue surrounding the sampling site remains mechanically fixed while obtaining the image, obtaining the tissue samples and examining the tissue samples.

7. The method according to claim 1, wherein the lateral sampling window of the core needle is a sampling window for a cylindrical tissue sample, wherein the lateral sampling window is rotated in a desired sampling direction and an angle of rotation versus a starting position is selected as a first coordinate for the first sample set.

8. The method according to claim 7, wherein an original distance before sampling, between the core needle and a sampling site parallel to the core needle is used as an additional coordinate.

9. The method according to claim 8, wherein a distance of an original sampling site from the core needle is determined from a number and thickness of the tissue samples already taken in this direction.

10. The method according to claim 7, wherein changes of the at least one parameter are measured along a longitudinal axis in the cylindrical tissue sample that was taken, and a position on the longitudinal axis is associated with each measurement value.

11. The method according to claim 10, wherein a three-dimensional dataset is obtained from the first coordinate and a second coordinate, the second coordinate being a position along the longitudinal axis of the tissue sample and the first coordinate being a penetration depth of the core needle, and is used for graphic representation of a distribution of tissue properties characterized by measured parameter or parameters.

12. The method according to claim 11, wherein grayscales or color codes are used for a graphic representation of the measured parameter or parameters.

13. The method according to claim 1, wherein the tissue samples are taken according to a spatially systematic procedure and are serially aspirated into a tube or a chambered system, thereby achieving an ordered state that represents at least one part of an association process to a sampling site.

14. The method according to claim 1, wherein the tissue alteration that may be present is recognized or measured by measuring a parameter that represents a tissue property of an altered metabolism.

15. The method according to claim 1, further comprising labeling the first sample set before or during the examining for the at least one parameter.

16. The method according to claim 15, wherein the marker comprises a marker with which a localization of the tissue alteration is possible even before taking the tissue samples.

17. The method according to claim 16, wherein the marker comprises an organometallic complex.

18. The method according to claim 1, wherein the marker is directly recognizable and measurable visually and/or has a primary radiation or an excited secondary radiation.

19. The method according to claim 18, wherein a fluorescent radiation is initiated to detect the tissue alteration.

20. The method according to claim 1, wherein the marker comprises luminescent or fluorescent bacteria or viruses, which are not only concentrated in the altered tissue but also can reproduce themselves.

21. The method according to claim 20, wherein the marker comprises a gadolinium chelate complex or metalloporphyrins for producing a systemic agent for fluorescence labeling.

22. The method according to claim 1, wherein a safety margin of tissue with no alteration detected is subsequently taken in all directions.

23. The method according to claim 1, wherein the taking and examining the first sample set of tissue samples and the additional tissue samples is performed using a device, the device comprising:
- a sampling device that is constructed such that the sampling device enables a spatially associable taking of tissue samples; and
- an examination unit that is constructed for examination of tissue samples immediately after the tissue samples are taken by the sampling device, the examination unit examining for selected parameters.

24. The method according to claim 23, the device further comprising a controller that causes the taking of additional tissue samples to be adjusted as a function of a program and/or of results of the examination of the first sample set of tissue samples for selected parameters.

25. The method according to claim 23, the device further comprising a supply device for supplying tissue samples from the sampling device to the examination unit while the surgical procedure is still occurring.

26. The method according to claim 23, wherein the examination unit comprises a detector for determining a measurement value of a parameter typical of a tissue alteration.

27. The method according to claim 23, wherein the sampling device is constructed for taking cylindrical tissue samples, wherein the examination unit can ascertain tissue alterations inside the tissue samples by a detector with a one-dimensional position resolution along a longitudinal axis.

28. The method according to claim 23, the device further comprising:
- a storage unit to store a dataset of measurement values, wherein the measurement values are determined by the examination unit and are associated with a respective defined sampling site for each tissue sample; and
- an output device comprising a printer or a monitor for graphic representation of the spatial distribution of the measurement values.

29. The method according to claim 28, the device further comprising:
- a controller that causes the taking of additional tissue samples to be adjusted as a function of a program and/or of results of the examination for tissue samples for selected parameters; and
- an input device for inputting parameters for the controller.

30. The method according to claim 23, wherein the examination unit comprises a radiation source for exciting fluorescent light.

31. The method according to claim 23, the device further comprising a radiation source for short-wavelength light that can be introduced through a core needle for generating a fluorescence at the sampling site.

32. The method according to claim 23, the device further containing a heat source that can be introduced through a core needle for local application of heat at the sampling site.

33. The method according to claim 23, wherein the device is constructed for systematic deposition or storage of the tissue samples.

34. The method according to claim 1, wherein taking additional tissue samples comprises using the core needle without removing it from the altered tissue.

35. The method according to claim 1, wherein each tissue sample is less than or equal to about 2 cm in diameter.

* * * * *